United States Patent

Berger et al.

[11] Patent Number: 5,596,061
[45] Date of Patent: Jan. 21, 1997

[54] ORGANOSILICONE HAVING A CARBOXYL FUNCTIONAL GROUP THEREON

[75] Inventors: Abe Berger, Summit; Dennis L. Fost, Ridgewood, both of N.J.

[73] Assignee: Mona Industries, Inc., Paterson, N.J.

[21] Appl. No.: 420,746

[22] Filed: Apr. 12, 1995

Related U.S. Application Data

[63] Continuation-in-part of Ser. No. 298,565, Aug. 31, 1994, abandoned, and Ser. No. 174,660, Dec. 28, 1993, abandoned.

[51] Int. Cl.$^6$ .................................................. C08G 77/04
[52] U.S. Cl. ............................. 528/26; 528/25; 528/38; 548/406
[58] Field of Search .............................. 528/25, 26, 38; 548/406

[56] References Cited

U.S. PATENT DOCUMENTS

| | | |
|---|---|---|
| 3,113,139 | 12/1963 | Birum et al. . |
| 3,389,160 | 6/1968 | Reid . |
| 3,890,269 | 6/1975 | Martin . |
| 4,006,176 | 2/1977 | Heckert . |
| 4,026,880 | 5/1977 | Mitchell . |
| 4,045,460 | 8/1977 | Kleinstück . |
| 4,104,296 | 8/1978 | Pike . |
| 4,185,087 | 1/1980 | Morlino . |
| 4,234,502 | 11/1980 | Kappler et al. . |
| 4,282,366 | 8/1981 | Eudy . |
| 4,342,742 | 8/1982 | Sebag et al. . |
| 4,384,130 | 5/1983 | Martin . |
| 4,417,066 | 11/1983 | Westall . |
| 4,511,727 | 4/1985 | Martin . |
| 4,654,161 | 3/1987 | Kollmeier et al. . |
| 4,847,397 | 7/1989 | Sawaragi et al. . |
| 4,866,192 | 9/1989 | Plueddemann et al. . |
| 4,889,942 | 12/1989 | Gutek et al. . |
| 4,891,166 | 2/1990 | Schoaefer et al. . |
| 4,898,614 | 2/1990 | Halloran et al. . |
| 4,983,384 | 1/1991 | O'Lenick, Jr. . |
| 4,996,342 | 2/1991 | Ching et al. . |
| 5,008,424 | 4/1991 | Halloran et al. . |
| 5,039,761 | 8/1991 | Ono et al. . |
| 5,068,377 | 11/1991 | Kawamolo et al. . |
| 5,084,577 | 1/1992 | Bolich, Jr. . |
| 5,087,715 | 2/1992 | Snow . |
| 5,117,024 | 5/1992 | Dinhet et al. . |
| 5,151,210 | 9/1992 | Stevri et al. . |

*Primary Examiner*—Melvyn I. Marquis
*Attorney, Agent, or Firm*—Franklyn Schoenberg

[57] ABSTRACT

A polysiloxane composition is provided having the formula

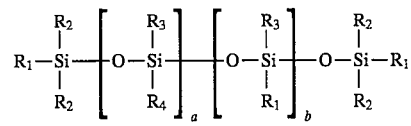

wherein:

$R_1$, can be $R_2$ or at least one pyrrolidone containing group of the general formula:

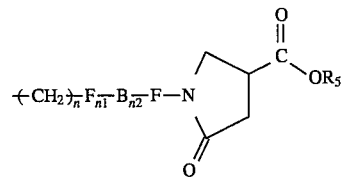

wherein; $R_5$ is hydrogen, lower alkyl or alkali metal; F, is linear or branched alkylene of 1–12 carbon atoms; n is 0 or 2; $n^1$ is 0 or 1; $n^2$ is 0 or 1; and B is —$NR_9$, sulfur or oxygen, wherein R, is hydrogen or lower alkyl; with the proviso that when n is 0 and $n^2$ is 1, $n^1$ is 1, when n is 2 and $n^2$ is 1, $n^1$ is 0 or 1 and when n is 2 and $n^2$ is 0, $n^1$ is 0;

$R_2$ is selected from alkyl, aryl and olefinic (vinyl);

$R_3$ and $R_4$, are selected from alkyl, aryl, capped or uncapped polyoxyalkylene, alkaryl, aralkylene or alkenyl;

a is an integer from 0 to 50,000; and b is an integer from 0 to 100.

15 Claims, No Drawings

ORGANOSILICONE HAVING A CARBOXYL FUNCTIONAL GROUP THEREON

RELATED APPLICATION

This application is a continuation-in-part of application Ser. No. 08/298,565, filed Aug. 31, 1994 and application Ser. No. 08/174,660, filed Dec. 28, 1993, both now abandoned.

FIELD OF THE INVENTION

The present invention relates to novel organosilicone compositions and, more particularly, to silicone compositions having a carboxyl functional group thereon.

BACKGROUND OF THE INVENTION

While carboxyl functional organosilicones are known, they are generally difficult and expensive to prepare and the commercial use thereof has therefore been limited. Heretofore, no convenient method for directly preparing polysiloxanes containing functional carboxylic acid groups is known and indirect routes for their preparation have generally been used, including hydrosilylation of an unsaturated ester followed by hydrolysis, or alternatively, by hydrolysis of nitrile-containing silicone fluids. However, polysiloxanes containing one or more functional groups such as amino groups are well known and readily available and have been used in a variety of commercial applications. Accordingly, the development of a method for readily and more directly preparing polysiloxanes containing one or more functional carboxyl groups would be desirable and it would be particularly advantageous if such method employed readily available materials such as amino functional polysiloxanes for not only preparing carboxyl functional polysiloxanes but a variety of organosilicone derivatives thereof as well, including silicone containing compositions which are readily soluble in a variety of solvents, preferably soluble in water such as silicone-containing phospholipid compositions and the like.

While, as indicated, polysiloxanes containing functional carboxylic acid groups and methods for preparing the same have heretofore been suggested, there is no disclosure or suggestion of the novel carboxyl functional silicone compositions described in copending application Ser. No. 174,660 filed Dec. 28, 1993 and application Ser. No. 298,565 filed Aug. 31, 1994 (now both abandoned) of which the present application is continuation in part or of the novel carboxyl functional silicone compositions of the present invention.

SUMMARY OF THE INVENTION

It is accordingly an object of the present invention to provide novel organosilicone compositions having at least one carboxyl functional group thereon.

It is another object of the present invention to provide a method for directly and readily preparing organosilicone compositions having at least one carboxyl functional group thereon.

In accordance with the present invention, there has now been discovered novel polysiloxanes containing one or more carboxylic acid groups and/or the ester derivatives thereof that may be represented by the following general formula:

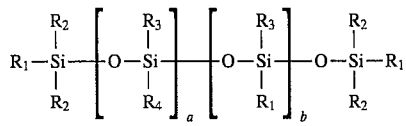

wherein:

$R_1$, which can be the same or different, can be selected from $R_2$, H, a primary amine containing group, and a pyrrolidone containing carboxyl functional group of the formula:

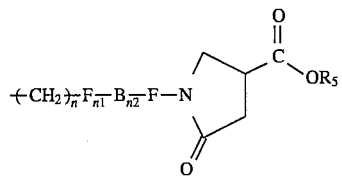

wherein at least one of $R_1$ is a pyrrolidone containing carboxyl or ester functional group or salt derivative thereof as shown; F, which can be the same or different, is linear or branched alkylene of 1–12 carbon atoms; $R_2$ is as defined below; $R_5$ can be hydrogen, lower alkyl ($C_{1-6}$) or alkali metal; n is zero or 2; $n^1$ is zero or 1; $n^2$ is zero or 1; and B is —$NR_9$, sulfur (S) or oxygen (O), wherein $R_9$ is hydrogen or lower alkyl ($C_{1-6}$), with the proviso that when n is 0 and $n^2$ is 1, $n^1$ is 1, when n is 2 and , $n^2$ is 1, $n^1$ is 0 or 1 and when n is 2 and $n^2$ is 0, $n^1$ is 0;

$R_2$ can be the same or different and can be selected from alkyl, aryl and olefinic (vinyl);

$R_3$ and $R_4$, which may be the same or different, are selected from alkyl, aryl, capped or uncapped polyoxyalkylene, alkaryl, aralkylene and alkenyl (vinyl);

a can be an integer from 0 to 50,000; and b can be an integer from 0 to 100.

In another aspect of the present invention there is provided a method for preparing polysiloxanes containing one or more carboxylic acid pyrrolidone groups and/or the ester derivatives thereof, which comprises reacting an organosilicone fluid or composition having at least one primary amine functional group with itaconic acid or an ester thereof at an elevated temperature (preferably from about 90° C. to about 150° C.) for a time sufficient to react, preferably substantially completely react (generally ranging from about 1–5 hours), the itaconic and or ester thereof with the functional primary amine group(s) on the silicone fluid or composition to form an organosilicone composition having at least one pyrrolidone-containing carboxyl functional group.

In yet another aspect of the present invention there is provided an alternate method for preparing polysiloxanes containing one or more ester derivatives of carboxylic acid pyrrolidone groups which comprises reacting an organosilicone fluid or composition having one or more hydride groups (terminal or lateral) on the polysiloxane chain with an N-alkenyl carboalkoxy containing a pyrrolidone nucleus portion in the presence of a noble metal catalyst, preferably soluble platinum catalyst, at an elevated temperature (preferably between about 65° C. and 130° C.) for the time sufficient to react, preferably substantially completely react, the hydride groups on the silicone fluid or composition with the pyrrolidone group.

In a still further aspect of the present invention there is provided a novel silicone-modified amidoamine composition having the formula:

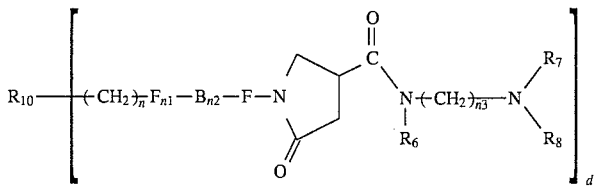

wherein:
- $R_{10}$ is the silicone backbone chain as herein described to which at least one pyrrolidone containing amidoamine derivative of a carboxyl functional group can be attached as shown;
- $R_6$ is hydrogen or alkyl, hydroxyalkyl or alkenyl of up to 6 carbon atoms each, or cycloalkyl of up to 6 carbon atoms, or polyoxyalkylene of up to 10 carbon atoms within the oxyalkylene unit;
- $R_7$ and $R_8$, which may be the same or different, are selected from alkyl, hydroxyalkyl, carboxyalkyl of up to 6 carbon atoms in each alkyl; and polyoxyalkylene of up to 10 carbon atoms; in addition $R_7$ and $R_8$ taken together with the nitrogen to which they are attached may represent an N-hetercycle.
- n is 0 or 2;
- $n^1$ is zero or 1;
- $n^2$ is zero or 1;
- $n^3$ is an integer from 2 to 12;
- B is $-NR_9$, sulfur or oxygen, wherein $R_9$ is hydrogen or lower alkyl ($C_{1-6}$); with the proviso that when n is 0 and $n^2$ is 1, $n^1$ is 1, when n is 2 and $n^2$ is 1, $n^1$ is 0 or 1, and when n is 2 and $n^2$ is 0, $n^1$ is 0;
- F, which may be the same or different is branched or linear alkylene of 1–12 carbon atoms; and
- d is at least one.

DESCRIPTION OF THE PREFERRED EMBODIMENTS

In accordance with the present invention there are provided novel polysiloxanes comprising a class of carboxyl functional polysiloxanes which may be represented by the general formula:

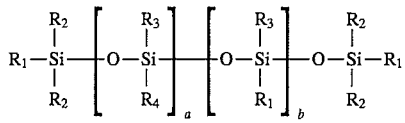

wherein:
- $R_1$, which can be the same or different, can be selected from $R_2$, H, a primary amine containing group and a pyrrolidone containing carboxyl functional group of the general formula:

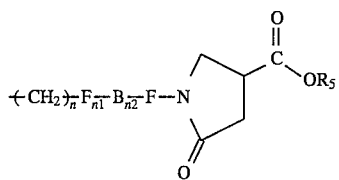

wherein at least one $R_1$ is a pyrrolidone-containing carboxyl or ester functional group or salt derivative thereof as shown; F, which can be the same or different, is linear or branched alkylene of 1–12 carbon atoms; $R_2$ is as defined below; $R_5$ is hydrogen, alkyl, preferably lower alkyl ($C_{1-6}$), or an alkali metal; n is 0 or 2; $n^1$ is 0 or 1; $n^2$ is 0 or 1; and B is $-NR_9$, sulfur (S) or oxygen (O), wherein $R_9$ is hydrogen or lower alkyl ($C_{1-6}$); with the proviso when n is 0 and $n^2$ is 1, $n^1$ is 1, when n is 2 and $n^2$ is 1, $n^1$ is 0 or 1 and when n is 2 and $n^2$ is 0, $n^1$ is 0;

- $R_2$ can be the same or different and can be selected from alkyl, aryl and olefinic (vinyl);
- $R_3$ and $R_4$, which may be the same or are selected from alkyl, aryl, capped or uncapped polyoxyalkylene, alkaryl, aralkylene and alkenyl (vinyl);
- a can be an integer from 0 to 50,000;
- b can be an integer from 0 to 100;

It is evident from the general formula above that the polysiloxane compositions of the present invention have one or more pyrrolidone containing functional carboxyl or ester group(s) or salt derivative thereof linked terminally, laterally or both terminally and laterally to the silicone (polysiloxane) chain through a hydrocarbon linkage which may contain a hetero atom.

The polysiloxane compositions according to the present invention are useful, for example, for reducing the friction of petroleum flow through pipelines as well as being precursors for a wide range of personal care products, fiber treating agents and the like which impart such advantages as improved feel, substantivity, reduced surface tension, and anti-stick characteristics.

The novel carboxyl functional polysiloxanes of the present invention surprisingly and unexpectedly can be readily and directly prepared by the reaction of corresponding silicone compositions or fluids having one or more functional primary amine groups with up to about one equivalent, preferably about stoichiometric quantities, of itaconic acid or its ester per functional primary amine group(s) at an elevated temperature for the time sufficient for substantially all of the itaconic acid or its ester to react with the functional primary amine group(s). In general from about 0.5, preferably, from about 0.9 to about 1.1 equivalents of itaconic acid or its ester per functional primary amine group is reacted with the silicone fluid wherein substantially all the itaconic acid and preferably all the functional primary amine group(s) are reacted and polysiloxane compositions with at least one pyrrolidone containing functional carboxyl group(s) and/or its ester are formed.

The reaction can be carried out neat or in an inert solvent such as alcohol, hydrocarbon solvent, chlorinated hydrocarbon and the like, as desired, in general, at elevated temperature, preferably from about 90° C. to about 130° C. The reaction proceeds readily and generally complete reaction of the itaconic acid or its ester with the available functional primary amine groups will occur in from about 1 to 5 hours, with routine analytical techniques for amine and acid values as well as monitoring water and/or alcohol evolution being used to determine completion of the reaction.

Primary amine functional silicone fluids suitable for use in accordance with the practice of the invention, having one or more primary amine functional group(s) linked terminally, laterally or both terminally and laterally, as desired, are well known and are available commercially, for example, from Dow Corning, Th. Goldschmidt AG and Shin-Etsu. While the equivalent weight of the silicone fluids or compositions which may be employed in the preparation of the polysiloxanes of the present invention is not critical, and suitable compositions may have equivalent weights of 5,000 to 10,000 or even higher, silicone fluids having equivalent weights from about 500 to about 5,000 are in general preferred.

As indicated, the polysiloxane compositions of the present invention are readily prepared by reaction of primary amine functional silicone fluids with itaconic acid or its ester. Itaconic acid (methylene succinic acid) is a compound of the formula:

$$CH_2=C(COOR_9)CH_2COOR_9$$

wherein $R_9$, which can be the same or different, is hydrogen or lower alkyl (1–6 carbon atoms).

The compound itaconic acid is available commercially from Pfizer Chemicals Division whereas ester derivatives thereof are available from Morflex Inc., Greensboro, N.C. The compounds are produced by known fermentation techniques although chemical synthesis methods are also known.

The novel carboxyl functional polysiloxanes, or ester derivatives thereof, of the present invention can also be readily prepared by a hydrosilylation reaction wherein a silicone fluid or composition having one or more hydride substituents on the silicone chain (terminal, lateral or combination or terminal and lateral) is added to a N-alkenyl carboalkoxy containing pyrrolidone nucleus in the presence of a noble metal (Group VIII metal) catalyst, preferably soluble platinum, at an elevated temperature (65° C. to 130° C.) for a time sufficient for substantially all of the N-alkenyl carboalkoxy containing pyrrolidone to react with the hydride group(s). The N-alkenyl carboalkoxy containing pyrrolidone reactant can have a N-allyl or higher olefinic group of 3 or more carbon atoms which can also include at least one hetero atom. The reaction can be carried out neat or in inert solvents such as toluene, benzene, chlorobenzene, heptane and the like. In general, from about 0.5 up to about one equivalent, preferably from about 0.9 to about 1.1 equivalents of the N-alkenyl pyrrolidone groups per functional hydride groups is reacted with the silicone fluid wherein substantially all the N-alkenyl carboalkxy containing pyrrolidone and, preferably all of the functional hydride groups are reacted. Suitable platinum catalysts include solubilized platinum or platinum metal on inert supports such as alumina, charcoal and the like. In general from about $10^{-3}$ to $10^{-6}$ moles of platinum per mole of hydride group can be used. In another aspect of the present invention, there are provided novel silicone-containing amidoamines suitable for use as a surfactants and a variety of other applications as well as intermediate reactants which are preferably derivatives of the novel polysiloxane compositions of the invention as hereinabove described. The novel amidoamine compositions of the invention may be represented by the general formula:

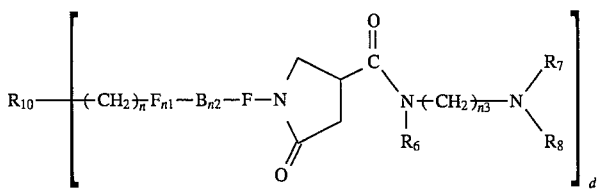

wherein:

$R_{10}$ is a silicone backbone chain as herein described to which at least one pyrrolidone containing carboxyl functional group or amidoamine derivative thereof is attached as hereinabove shown;

$R_6$ is hydrogen or alkyl, hydroxyalkyl or alkenyl up to 6 carbon atoms each, cycloalkyl of up to 6 carbon atoms or polyoxyalkylene of up to 10 carbon atoms, preferably from 2 to 5 carbon atoms, within the oxyalkylene unit and at least one $R_6$ is hydrogen;

$R_7$ and $R_8$, which may be the same or different, are selected from alkyl, hydroxyalkyl, carboxyalkyl of up to 6 carbon atoms in each alkyl, and polyoxyalkylene of up to 10 carbon atoms; in addition $R_7$ and $R_8$ taken together with the nitrogen to which they are attached may represent N-heterocycle.

F, which can be time same or different is linear or branched alkylene of 1–12 carbon atoms;

B is —$NR_9$, sulfur or oxygen, wherein $R_9$ is hydrogen or lower alkyl ($C_{1-6}$); with the proviso that when n is 0 and $n^2$ is 1, $n^1$ is 1, when n is 2 and $n^2$ is 1, $n^1$ is 0 or 1, and when n is 2 and $n^2$ is 0, $n^1$ is 0;

n is 0 or 2;

$n^1$ is zero or 1;

$n^2$ is zero or 1;

$n^3$ is an integer from 2 to 12;

d is an integer from 1 or greater, generally from 1–50 and preferably 2–10.

The novel silicone-containing amidoamine compositions of time invention can be prepared as follows:

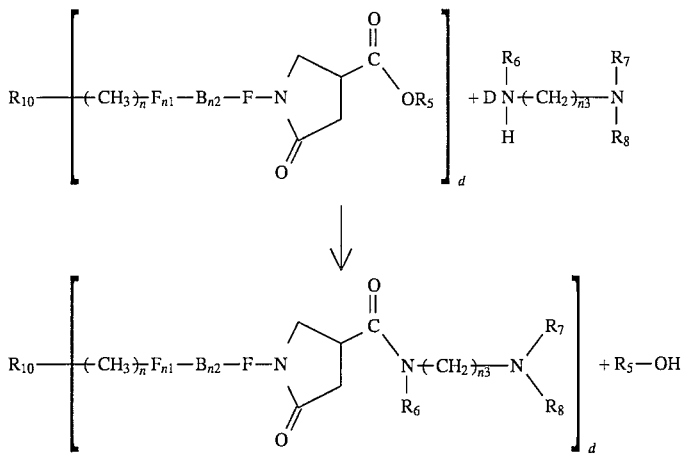

wherein:

$R_{10}$ is a silicone backbone chain as herein described to which at least one pyrrolidone containing carboxyl functional group or amidoamine derivative thereof is attached as hereinabove shown;

$R_5$ is hydrogen, lower alkyl ($C_{1-6}$) or alkali metal;

$R_6$ is hydrogen or alkyl, hydroxyalkyl or alkenyl up to 6 carbon atoms each, cycloalkyl of up to 6 carbon atoms or polyoxyalkylene of up to 10 carbon atoms, preferably from 2 to 5 carbon atoms, within the oxyalkylene unit and at least one $R_6$ is hydrogen;

$R_7$ and $R_8$, which may be the same or different, are selected from alkyl, hydroxyalkyl, carboxyalkyl of up to 6 carbon atoms in each alkyl, and polyoxyalkylene of up to 10 carbon atoms; in addition $R_7$ and $R_8$ taken together with the nitrogen to which they are attached may represent an N-heterocycle.

F, which can be the same or different is linear or branched alkylene of 1–12 carbon atoms;

B is —$NR_9$, sulfur or oxygen, wherein $R_9$ is hydrogen or lower alkyl; with the proviso that when n is 0 and $n^2$ is 1, $n^1$ is 1, when n is 2 and $n^2$ is 1, $n^1$ is 0 or 1, and when n is 2 and $n^2$ is 0, $n^1$ is 0;

n is 0 or 2;

$n^1$ is zero or 1;

$n^2$ is zero or 1;

$n^4$ is an integer from 2 to 12;

d and D is an integer from 1 or greater, generally from 1–50 and preferably 2–10. The reactant ratio of the amine reactant to the carboxyl reactant on the silicon is preferably 1:1 but can be varied in ratio from 1:0.8 to 1:1.2.

Silicone-containing amidoamines of the invention are readily prepared by the above coupling reaction from the novel polysiloxane compositions of the present invention having one or more pyrrolidone containing functional carboxyl group(s) as hereinabove described.

The above coupling reaction for preparing the silicone-containing amidoamine compositions can be carried out neat or can be carried out in an inert solvent such as xylene, toluene, chlorobenzene or the like. While the equivalent weight of the silicone-containing amidoamine compositions is not critical, preferably the equivalent weight of such compositions are from about 500 to 1500.

The preparation of specific compositions of the invention is illustrated by the following specific examples which are provided herein for purposes of illustration only and are not intended to limit the scope therein.

EXAMPLE 1

An alpha-omega diamino functional polysiloxane fluid obtained commercially under the designation Tegomer A-Si2120 from Goldschmidt Company is used in this example. The amine content of the fluid is 3.5% which corresponds to a molecular weight of 91.4 grams of the above polysiloxane fluid (0.1 moles) is admixed with 26 grams (0.2 moles) of Itaconic Acid in a reaction vessel. Upon combination of the reactants, a heterogeneous mixture is formed. External heat is applied to the reaction vessel bringing the reaction mixture to a temperature of about 110° C., whereupon the reaction mixture becomes completely homogeneous while the temperature rises to 140° C.

After a heating period of 4 hours, a total of 7.5 ml of volatiles are collected. The acid value of the reaction mixture is 81.6 (theoretical 95.5) while the alkali number is nil, thus confirming that there is the presence of carboxyl groups on the product.

EXAMPLE 2

An alpha, omega-Bis primary amino alkyl dimethyl polysiloxane fluid with an average molecular weight about 1579.5 and having the general formula:

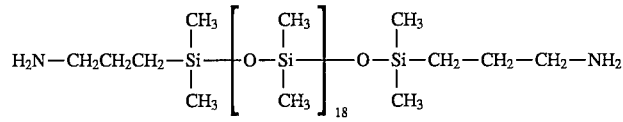

obtained commercially from Shin-Etsu under the designation X-22161A is used in this example.

A mixture of 994.5 grams of the above polysiloxane fluid (0.6296 moles) and 163.7 grams (1.25 moles) of Itaconic Acid is formed in a reaction vessel and heated (slowly to about 90° C. at which point an exotherm occurs raising the reaction vessel temperature to 130° C. and water starts to evolve.

The reaction mixture is heated to and maintained at a temperature of 140° C. to 150° C. for a period of 3 hours during which time about 20 ml. of water and other volatiles are collected. A clear, yellow viscous liquid is formed having an alkali number of 0.

The mixture is then cooled to 90° C. and 192.6 grams (an excess) of dimethylamino propylamine is admixed therewith. The temperature in the reaction vessel is increased to 170° C. to 185° C. and maintained at that temperature for an 4 additional hours during which time a total of 92 ml. of volatiles is collected.

The reaction mixture is then cooled to about 50° C. and subjected to a vacuum of 30 mm. While the vacuum is slowly drawn to 3 mm, the reaction vessel temperature is increased from 75° C. to 150° C. The product residue collected from the reaction vessel has a 92% yield with an alkali number of 67 (theoretical alkali number is 57).

200.88 grams of the reaction product above (0.12 moles) is then admixed with 75.4 grams of 40% active phosphate ester halide reactant and a 2:1 mixture of propylene glycol and water to obtain a solution having 30% solids. The phosphate ester halide reactant used is prepared by the reaction of 3 moles of epichlorohydrin and one mole of sodium dihydrogen phosphate.

The reaction admixture is heated for 4 hours at a temperature range of 75° C. to 85° C. whereupon a homogeneous, clear liquid solution is obtained having a NaCl content of 1.8% (theoretical NaCl is 1.86%).

The product formed when mixed with water produced a great deal of stable foam whereas the polysiloxane functional amino fluid used as a starting material in the example provided no foam when mixed with water.

EXAMPLE 3

Another sample of a diamino polysiloxane fluid such as used in example 2 is used in this example. The average molecular weight of the sample is 1729 which corresponds to a percent amine of 1.85%.

To 43.2 grams (0.025 moles) of the above siloxane fluid in a reaction vessel is added with mixing 6.5 grams (0.05 moles) of Itaconic acid. The mixture is heated to 90° C. whereupon an exotherm occurs raising the temperature to 130° C. and resulting in a liquified viscous yellow mass. The reaction mixture is heated to and maintained at a temperature of 135°–140° C. for 3 hours while some volatiles are collected and at which point the alkali number is zero.

There is then added to the reaction mixture 7.7 grams (0.075 moles, 50% excess) of dimethylamino propylamine (DMAPA) and the temperature is raised to 165° C. where it is held for four additional hours. The reaction mixture is subjected to vacuum stripping to remove excess DMAPA at a reaction vessel temperature of 125° C. and a vacuum of 10 mm. The alkali number of the reaction product residue is 54 (theoretical 52.9).

A combination of 21.2 grams (0.01 moles) of the reaction product above, 6.25 grams (0.0061 mole) of 40% active phosphate ester halide reactant prepared as in example 2, 16 grams of isopropanol and 16 grams of water having a solid content of 40% is prepared in a reaction 2 vessel. The combined reactants are heated to a temperature of 95° C. for four-five hours at which time a clear yellow solution is obtained having a NaCl content of 2.4% (theoretical 1.9%).

The product formed when added to water produces a great deal of stable foam.

EXAMPLE 4

A lateral (pendant) amino functional silicone fluid having an average molecular weight of about 3720 obtained from Shin-Etsu under the product designation KE-864 is used in this example.

A mixture of 377 grams (0.1013 moles) of the silicone fluid and 13.2 grams (0.1013 moles) of Itaconic acid is formed in a reaction vessel and heated to a temperature of 160° C. for about two hours.

A clear melt is formed having an acid number of 11.6 (theoretical 14.6).

EXAMPLE 5

A pendant (lateral) amino functional silicone fluid having an average molecular weight of 4400 obtained from Shin-Etsu under the product designation KF865 is used in this example.

88 grams (0.02 moles) of the silicone fluid is admixed with 2.6 grams of Itaconic acid (0.02 moles) and heated to a temperature of 130°–140° C. whereupon a clear melt is obtained and then continued heating for an additional two hours.

After heating for two hours, the reaction mixture is cooled to 70° C. and 4.08 grams (an excess) of dimethylamino propyl amine (DMAPA) is admixed therewith. The reaction mixture is then heated to a temperature of 165° C. for four hours, cooled to 70° C. and vacuum stripped at 30–10 mm for three hours while slowly raising the temperature to 110° C.

The reaction product residue is a clear liquid having an alkali number of 12.3 (theoretical 12.2) and an acid number of 0. i.r. analysis confirms the presence of an amide linkage.

EXAMPLE 6

A pendant (lateral) amino functional silicone fluid obtained from Shin-Etsu under the product designation KF 865 is used in this example. The silicone fluid has an amine value of 0.2219 percent which corresponds to an amine equivalent weight of 5675.

665.9 grams (0.1173 equiv. wt.) of the silicone fluid and 15.25 grams of Itaconic acid (0.1173 mole) are combined with 150 ml of xylene in a reaction vessel and heated to a temperature of 130°–140° C. under reflux. After heating for 4 to 5 hours under reflux, 2.3 ml of water is removed (theory 2.1).

17.9 grams of dimethylpropyl amine (DMAPA) is then admixed with the reaction mixture and heated under reflux at a temperature of 160°–170° C. for a period of about 4 hours during which time an additional 2.1 grams of water is removed. The reaction mixture is cooled to about 70° C. and vacuum stripped at 30–40 mm to remove low boiling volatiles. A vacuum of 5–10 mm is then applied to the reaction mixture and the reaction vessel is heated for three hours at 140° C. The reaction product is a clear liquid having an alkali number of 9 (theoretical 9.55) which corresponds to an amine equivalent weight of 6233.

EXAMPLE 7

This example illustrates an alternate procedure of preparing a polysiloxane composition having at least one pyrrolidone containing carboxyl functional group(s).

A mixture of 122.4 grams of octamethylcyclotetrasiloxane, 13.4 grams of tetramethylohsiloxane, 0.7 grams of activated charcoal and 0.07 grams concentrated sulfuric acid are charged into a reaction vessel and heated with agitation to 65° C. for 24 hours. The mixture is filtered and the filtrate is subjected to reduced pressure at 70° C. for 48 hours. A colorless liquid is obtained having a number average molecular weight of about 1580 which is terminated in silicon hydride as determined by NMR.

A solution of 15.8 grams (0.1 mole) of dimethyl itaconate in 30 ml of methanol is added at ambient to a reaction vessel containing a solution of 5.7 grams (0.1 mole) alylamine in 10 ml methanol. Upon complete addition of the dimethyl itaconate, a mild exotherm is produced raising the reaction mixture temperature to 55° C. Following this, the reaction mixture is held at reflux for 3 hours. The reaction mixture is stripped of solvent and the product (N-allyl 4 carbon-methoxy pyrrolidone) is isolated by distillation of 115° C. A colorless liquid is obtained in 85% yield.

158 grams of the silicone hydride terminated polysiloxane material prepared above is charged to a reaction vessel and 1 ml of a 0.1 N chloroplatinic acid solution in tetrahydrofurane (THF) is added thereto. The reaction mixture is heated to 90°–95° C., the heat source is removed and 36.6 grams (0.2 Equivalents) of the itaconate/allylamine reaction product prepared above is added to the reaction vessel. After a brief induction period, the temperature of the mixture starts to rise slowly and the reaction temperature is controlled between 110°–115° C. by the rate of addition. Following complete addition of the pyrrolidone reaction product, the reaction mixture is heated at 120° C. for 3 hours.

Analysis of the reaction product indicates complete absence of Silicone-Hydride absorption and allylic unsaturated is also absent. NMR analysis confirms that the resulting reaction product is an alpha-Omega capped carbomethoxy pyrrolidone containing silicone fluid.

Although some preferred embodiments have been described, many modifications and variations may be made thereto in light of the above teachings. It is therefore to be understood that within the scope of the appended claims, the invention may be practiced otherwise than as specifically described and illustrated.

What is claimed is:

1. A polysiloxane composition having the formula

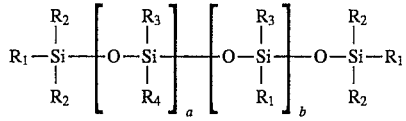

wherein:

$R_1$, which can be the same or different, is selected from $R_2$, H, a primary amine containing group or a pyrrolidone containing group of the general formula:

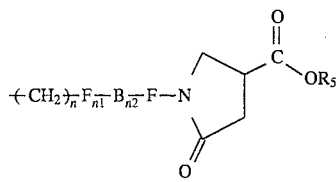

wherein at least one $R_1$ is a pyrrolidone containing carboxyl functional group or ester derivative thereof as shown; $R_2$ is as defined below; $R_5$ is hydrogen, lower alkyl ($C_{1-6}$) or alkali metal; F, which can be the same or different, is linear or branched alkylene of 1–12 carbon atoms; n is 0 or 2; $n^1$ is 0 or 1; $n^2$ is 0 or 1; and B is —$NR_9$, sulfur or oxygen, wherein $R_9$ is hydrogen or lower alkyl ($C_{1-6}$); with the proviso that when n is 0 and $n^2$ is 1, $n^1$ is 1, when n is 2 and $n^2$ is 1, $n^1$ is 0 or 1 and when n is 2 and $n^2$ is 0, $n^1$ is 0;

$R_2$ can be the same or different and is selected from alkyl, aryl or olefinic;

$R_3$ and $R_4$, which may be the same or different are selected from alkyl, aryl, capped or uncapped polyoxyalkylene, alkaryl, aralkylene or alkenyl;

a is an integer from 0 to 50,000; and b is an integer from 0 to 100.

2. The polysiloxane composition as claimed in claim 1, wherein $R_5$ is hydrogen or lower alkyl.

3. The polysiloxane composition as claimed in claim 1, wherein $R_1$ is $R_2$ or a pyrrolidone containing carboxyl functional group or ester derivative thereof.

4. The polysiloxane composition as claimed in claim 1, wherein at least one terminally linked $R_1$ group is a pyrrolidone containing carboxyl functional group or ester derivative thereof.

5. The polysiloxane composition as claimed in claim 1, wherein $R_3$ and $R_4$ are methyl and a is at least 1.

6. The polysiloxane composition as claimed in claim 1, wherein both terminal $R_1$ groups are $R_2$ and a and b are each at least 1.

7. The polysiloxane composition as claimed in claim 1, wherein $R_2$, $R_3$ and $R_4$ are methyl.

8. The polysiloxane composition as claimed in claim 1, wherein B is —$NR_9$, $n^1$ is 1, $n^2$ is 1 and n is 0.

9. A method for preparing polysiloxane compositions containing at least one pyrrolidone containing carboxyl functional group and/or the ester derivatives thereof, which comprises reacting an organosilicone composition having at least one primary amine functional group with itaconic acid or an ester derivative thereof at an elevated temperature for a time sufficient to react substantially all the itaconic acid or ester derivative thereof with the functional primary amine group(s) on the silicone composition to form an organosilicone composition having at least one pyrrolidone containing carboxyl functional group.

10. The method for preparing polysiloxane compositions as claimed in claim 9, wherein said organosilicone composition having at least one primary amine functional group is substantially compatible with said itaconic acid or ester derivative thereof and forms a homogeneous reaction mixture therewith.

11. The method for preparing polysiloxane compositions as claimed in claim 9, wherein reaction of said organosilicone composition having at least one primary amine functional group and itaconic acid or ester is carried out at a temperature from about 90° C. to about 130° C.

12. The method for preparing polysiloxane compositions as claimed in claim 9, wherein about a stoicteometric amount of itaconic acid or its ester derivative per functional primary group(s) is employed in said reaction.

13. The method for preparing polysiloxane compositions as claimed in claim 9, wherein said organosilicone composition has one or more terminal or laterial primary amine functional groups.

14. A method for preparing polysiloxane compositions containing at least one ester derivative of a pyrrolidone containing functional group which comprises reacting by hydrosilation an organosilixone fluid or composition having one or more hydrogen atoms directly bonded to a terminal silicon atom or hydrogen atoms directly bonded to a lateral silicon atom on the polysiloxane chain with an N-alkenyl carboalkyoxy containing a pyrrolidone nucleus portion in the presence of a noble metal catalyst at an elevated temperature for a time sufficient to react the hydrogen atom directly bonded to a silicon atom on said silicone fluid with the pyrrolidone group.

15. Silicone-modified amidoamine composition having the formula:

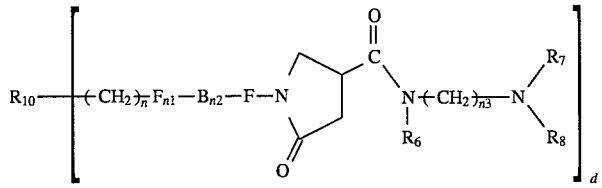

wherein:

$R_{10}$ is the silicone backbone chain to which at least one pyrrolidone containing amidoamine derivative of a carboxyl functional group as shown is attached;

$R_6$ is hydrogen or alkyl, hydroxyalkyl or alkenyl of up to 6 carbon atoms each, or cycloalkyl of up to 6 carbon atoms, or polyoxyalkylene of up to 10 carbon atoms within the oxyalkylene unit;

$R_7$ and $R_8$, which may be the same or different, are selected from alkyl, hydroxyalkyl, cycloalkyl or carboxyalkyl of up to 6 carbon atoms in each alkyl or polyoxalkylene of up to 10 carbon atoms; or in addition $R_7$ and $R_8$ taken together with the nitrogen to which they are attached can represent an N-heterocycle;

F which can be the same or different is linear or branched alkylene of 1–12 carbon atoms;

n is 0 or 2;

$n^1$ is 0 or 1;

$n^2$ is 0 or 1;

$n^3$ is at least 1;

B is —$NR_9$, sulfur or oxygen, wherein $R_9$ is hydrogen or lower alkyl; with the proviso that when n is 0 and $n^2$ is 1, $n^1$ is 1, when n is 2 and $n^2$ is 1, $n^1$ is 0 or 1 and when n is 2 and $n^2$ is 0, $n^1$ is 0; and d is at least one.

* * * * *